United States Patent
Dong et al.

(10) Patent No.: US 11,612,356 B2
(45) Date of Patent: Mar. 28, 2023

(54) ON-DIAPER BODY FLUID SCREENING DEVICE AND ASSOCIATED METHOD

(71) Applicants: University College of Southeast Norway, Kongsberg (NO); Sensovann AS, Borre (NO)

(72) Inventors: Tao Dong, Kongsberg (NO); Nuno Miguel Matos Pires, Kongsberg (NO); Zhaochu Yang, Borre (NO); Chaohao Chen, Borre (NO); Kai Dong, Borre (NO); Torill Lønningdal, Kongsberg (NO); Haakon Karlsen, Kongsberg (NO)

(73) Assignees: University College of Southeast Norway, Kongsberg (NO); Sensovann AS, Borre (NO)

( * ) Notice: Subject to any disclaimer, the term of this patent is extended or adjusted under 35 U.S.C. 154(b) by 1179 days.

(21) Appl. No.: 16/093,553

(22) PCT Filed: Apr. 10, 2017

(86) PCT No.: PCT/EP2017/058520
§ 371 (c)(1),
(2) Date: Oct. 12, 2018

(87) PCT Pub. No.: WO2017/178417
PCT Pub. Date: Oct. 19, 2017

(65) Prior Publication Data
US 2019/0133524 A1    May 9, 2019

(30) Foreign Application Priority Data

Apr. 15, 2016 (NO) .................................... 20160626

(51) Int. Cl.
*A61B 5/00* (2006.01)
*A61F 13/84* (2006.01)
(Continued)

(52) U.S. Cl.
CPC ........ *A61B 5/6808* (2013.01); *A61B 5/14507* (2013.01); *A61B 5/207* (2013.01);
(Continued)

(58) Field of Classification Search
CPC ... A61B 5/6808; A61B 5/14507; A61B 5/207; A61B 10/007; A61B 2010/0003;
(Continued)

(56) References Cited

U.S. PATENT DOCUMENTS 5,312,379 A    5/1994 Rahe
5,707,818 A    1/1998 Chudzik et al.
(Continued)

FOREIGN PATENT DOCUMENTS

EP    0560099 A2    9/1993
EP    2990118 A1    3/2016
(Continued)

OTHER PUBLICATIONS

Krähenbühl, J.-D., et al., "Evaluation of a novel in-vitro diagnostic device for the detection of urinary tract infections in diaper-wearing children," Swiss Med Wkly, 142:w13560, May 4, 2012, URL: <https://smw.ch/article/doi/smw.2012.13560/>.
(Continued)

*Primary Examiner* — Dennis White
(74) *Attorney, Agent, or Firm* — Shackelford, Bowen, McKinley & Norton, LLP

(57) ABSTRACT

An on-diaper body fluid screening device (100), comprising a stack of the following sheets: a surface sheet (110) permeable to body fluid, a collection sheet (120) impervious to body fluid, a testing sheet (130), which is body fluid absorbent and provided with colorimetric assay reaction pads (131), and which is provided with a body fluid barrier network (132) forming body fluid channels (134) between an inlet section (135) and the colorimetric assay reaction
(Continued)

pads (131), a protection sheet (140) impervious to body fluid, and a transparent readout sheet (150), through which the assay reaction pads (131) are visible. The protection sheet (140) comprises pad receiving openings (142). The collection sheet (120) comprises an inlet hole (125) which is arranged over the inlet section (135). A swelling component (702) is arranged in association with the inlet hole (125) and an inlet hole closing member (601).

10 Claims, 6 Drawing Sheets

(51) Int. Cl.
*A61B 10/00* (2006.01)
*G01N 33/493* (2006.01)
*G01N 33/543* (2006.01)
*A61B 5/20* (2006.01)
*G01N 33/52* (2006.01)
*A61B 5/145* (2006.01)

(52) U.S. Cl.
CPC ............ *A61B 10/007* (2013.01); *A61F 13/84* (2013.01); *G01N 33/493* (2013.01); *G01N 33/525* (2013.01); *G01N 33/543* (2013.01); *A61B 2010/0003* (2013.01); *A61F 2013/8473* (2013.01)

(58) Field of Classification Search
CPC .. A61B 5/145; A61F 13/84; A61F 2013/8473; A61F 5/44; G01N 33/493; G01N 33/525; G01N 33/543; G01N 33/50
See application file for complete search history.

(56) References Cited

U.S. PATENT DOCUMENTS

| | | |
|---|---|---|
| 6,981,951 B1 | 1/2006 | Rahe |
| 8,377,710 B2 | 2/2013 | Whitesides et al. |
| 2008/0269707 A1 | 10/2008 | Song |
| 2009/0155122 A1 | 6/2009 | Song |
| 2011/0123398 A1 | 5/2011 | Carrilho et al. |
| 2013/0084630 A1 | 4/2013 | Rolland et al. |
| 2013/0128036 A1* | 5/2013 | Whitesides ....... B01L 3/502715 348/135 |
| 2014/0121487 A1 | 5/2014 | Faybishenko et al. |
| 2016/0054229 A1* | 2/2016 | Jia ...................... G01N 21/8483 702/19 |

FOREIGN PATENT DOCUMENTS

| | | |
|---|---|---|
| WO | WO-2003005946 A1 | 1/2003 |
| WO | WO-2014066913 A2 | 5/2014 |
| WO | WO-2014098695 A1 | 6/2014 |
| WO | WO-2015134820 A1 | 9/2015 |
| WO | WO-2016028497 A1 | 2/2016 |
| WO | WO-2016178608 A1 * | 11/2016 |
| WO | WO-20160178608 A1 | 11/2016 |

OTHER PUBLICATIONS

Diez Schlereth, D., "International Search Report," prepared for PCT/EP2017/058520, dated Aug. 4, 2017, four pages.

Grover, William H., "Diaper Detective," World Health Organization, Jan. 20, 2014, URL:https://www.nibib.nih.gov/sites/default/files/Diaper_System.pdf, seven pages.

Franco, M., "Diaper Detective Smart Pad Senses Dehydration, Infection," URL: https://www.cnet.com/news/diaper-detective-smart-pad-senses-dehydration-infection/[Jun. 23, 2017 11:04:49], three pages.

* cited by examiner pad receiving opening

ON-DIAPER BODY FLUID SCREENING DEVICE AND ASSOCIATED METHOD

The present invention relates to a device and method for screening and analyzing multiple diagnostic parameters or biomarkers from body fluids sampled on diapers.

Particularly, this invention relates to methods of realizing the screening and analysis device, and methods of using it. Specifically, the invention concerns the design and assembly of the different device sheets with detailed components.

BACKGROUND

The present invention provides a point-of-care "on diaper" detecting device. Diapers are often used by elderly patients and the diaper itself can function as a sampling tool for urine collection. For testing purposes, collecting enough urine from the elderly patients is often a painful and time-consuming procedure. The diaper-based test will thus be a convenient tool for early-stage detection of important disease agents present in body fluids.

The detection of disease markers and health parameters in human body fluids is commonly conducted by paper dipsticks, which often provides a qualitative result. For body fluid analysis, there are a number of commercially available dipsticks, for instance Bayer Multistix®, or Roche Combur-Test®. Although the commercial dipsticks are widely used, especially in urinalysis, their application to diapers is not feasible, and the collection of urine in bottles is still necessary to perform the test.

The incompatibility of the conventional dipsticks to diapers open the possibility of developing "on-diaper" devices that can simultaneously perform sample collection and subsequent detection. No painful and inconvenient sample collection in bottles is necessary.

Despite the recognizable value of body fluid collection and analysis devices for diapers, few types of these devices are currently available in the market. However, the Svenska Cellulosa Aktiebolaget SCA has recently started to commercialize an "on-diaper" diagnostic device, entitled TENA U-Test, for detecting two urinary tract infection parameters, leukocytes and nitrite. As stated in Krähenbühl et al. Swiss Med Wkly. 2012; 142:w13560, the U-Test method has been demonstrated to be simple to use, thanks to its pealing-out mechanism, and can be an alternative to cumbersome procedures of urine collection by the bag-method or clean-catch followed by dipstick test. Furthermore, it is reported that the detection result is valid up to 24 hours, and an upwards analysis by a medical professional is still required.

However, the U-Test method does not show practicability for a wider screening of body fluid biomarkers. The U-Test analysis is limited to only two body fluid biomarkers, making it unable for monitoring relevant more human diseases, such as chronic renal diseases, cardiovascular diseases, among others. An "on-diaper" device with a screening capability as the conventional dipsticks would be of greater interest.

Further, the U-Test device shows other challenges. An experiment has showed that the U-Test does not incorporate a skin-contacting tissue that remains dry after the urination on the diaper. The U-Test does not present a mechanism of increasing the efficiency of sample collection, especially when the urinated reach the end sides of the device.

Recently, Scanadu is developing a urine test kit targeting not only leukocytes and nitrite but also other biomarkers encountered in the traditional urine dipsticks, including glucose, protein, blood, bilirubin, urobilinogen, microalbumin, creatinine, ketone, vitamin C, specific gravity, and pH. This high-throughput urinalysis capability is supported by a smartphone application that conducts the readout. However, there is no reported amenability of this smartphone-ready urine test to diapers.

Another project in progress is the creation of a smart diaper targeting the detection of multiple urinary biomarkers, done by Pixie Scientific. This smart diaper incorporates a patch in its architecture, and a smartphone is used to scan a barcode to obtain the urinal data. This is a special diaper and the system is not compatible to any commercial or widely used diapers.

An object of the present invention may be to provide a passive body fluid screening and analysis device for common diapers. Publication EP0560099 discloses a device for determining and/or measuring or checking of chemical and biological parameters in liquid medium, especially urine, with the aid of at least one indicator. This reported device functions as a "check-up" card applicable to a clear plastic sheet of a disposable structure. The solution in EP 0560099 is described to be limited to urinary parameter testing, and the device itself does not have the function of urine collection.

Publication U.S. Pat. No. 5,707,818 reports a device and a method to simultaneously perform a plurality of immunoassays in order to detect the presence of respective analytes in a sample. This solution demonstrates a structure to conduct multiple parameter detection, and the invented device separates the readout zone from the reagent zone, which is placed downstream from the common origin site. However, the solution presented here incorporates both the readout and reagent zones into single chemical reaction pads.

WO2014098695 discloses a peelable device for receiving and testing voided body fluids. This body fluid test device is reported to be straightforwardly glued on top of an absorbent article. The solution according to the present invention may in some embodiments not exclusively require gluing of the device. Instead, the device can reversibly be attached by use of physical fastening components. Further, the peelable device described in WO2014098695 does not describe mechanisms of controlling the sample flow within the device before reaching the testing areas. Instead, the invention herein describes on/off mechanisms for controlling the sample flow before the reaction pads.

Publication US20080269707 also describes an absorbent-article attached device. The structure reported in US20080269707 makes use of the lateral flow mechanism as the driving force for the fluid samples. This unidirectional fluid flow mechanism is in contrast to the multi-directional diffusive flow-through mechanism according to some embodiments of the present invention. The device disclosed herein makes use of test porous sheets wherein the fluid sample is distributed all over the structure, with the fluid paths defined by the presence of fluid-impervious barriers patterned onto the porous sheets.

Pattern of fluid-impervious barriers onto porous but planar sheets are known from publication U.S. Pat. No. 8,377,710B2. In that solution, the assay regions are in the porous sheet. In embodiments of the present invention, the assay regions may not be part of the porous sheet. Further, U.S. Pat. No. 8,377,710B2 does not suggest incorporation of the test porous sheet with other supporting sheets, and reference to compatibility to absorbent articles and/or diapers is not presented.

For the sample flow arrangement, publication US20110123398 reports a tridimensional arrangement of a plurality of patterned porous, hydrophilic layers. This contrasts to the 2-D topology exploited in embodiments of the present invention for the sample flow.

Of relevance, WO2003005946 A1 shows a sanitary hygienic article or napkin with a functional diagnostic set comprising a number of testing strips. These testing strips are insulated from each other. However, each testing strip in WO2003005946 A1 has its own inlet hole, independent from the rest of testing strips. This arrangement does not ensure equal sample volume distribution among the insulated testing strips, which could affect the accuracy and sensitivity of the testing results. Furthermore, in the solution described in WO2003005946 A1, each strip card shall be removed from the diagnostic set to perform the test. Thus, effective on-diaper or on-napkin analyses cannot be performed by that diagnostic set.

Patent publication U.S. Pat. No. 6,981,951 discloses an on-diaper body fluid screening device for absorption and examination of voided urine. The device has a transparent readout sheet in the form of a front see-through foil, which creates a transparent area as viewing window. Behind the viewing window the indicators are arranged on an indicator holder. This device also has a collection sheet that is impervious to body fluid and that comprises an inlet hole, which is arranged over the inlet section.

European patent application publication EP2990118 describes a biomedical paper sensor configured to determine concentration of biological materials in fluids such as blood, urine and saliva. The paper sensor has hydrophobic barrier walls of wax, which penetrates through the entire paper thickness. Color of pre-deposited reagents can be captured by a smart phone camera and can be processed by an algorithm to calculate the concentration of each analyte in the sample.

US2009155122 describes a multi-layered detection device compatible to an absorbent article. That device includes a control layer placed on top of a sensing layer. That control layer is in fluid communication with the inlet of the device and incorporates a reagent capable of inhibiting the reaction at the sensing layer. The diffusive movement of the reagent from the control layer to the sensing layer inhibits the reactions and ensures that only the first urinated is tested. Testing the second urinated would bring inaccuracy to the testing results. This feature may also be considered in embodiments according to the present invention. However, in contrast with the chemical inhibition method described in US2009155122 which is only specific for esterase detection, the invention herein proposes physical method to ensure first urinated testing. The proposed mechanisms relates to swelling and expansion of substrate materials to seal flexible valves.

The Invention

According to the present invention, there is provided an on-diaper body fluid screening device comprising a stack of the following sheets
   a surface sheet, which is permeable to body fluid;
   a collection sheet, which is impervious to body fluid;
   a testing sheet, which is body fluid absorbent and which is provided with a plurality of colorimetric assay reaction pads, and which is provided with a body fluid barrier network forming body fluid channels between an inlet section and the colorimetric assay reaction pads;
   a protection sheet, which is impervious to body fluid; and
   a transparent readout sheet, through which the assay reaction pads are visible;

According to the present invention,
   the protection sheet comprises pad receiving openings;
   the collection sheet comprises an inlet hole which is arranged over the inlet section; and
   a swelling component is arranged in association with the inlet hole and an inlet hole closing member.

The swelling component may thus be configured to close the inlet hole with the inlet hole closing member.

Hence, a body fluid screening device is provided, which will retain the body fluid in a non-dry state for several hours after entering of the body fluid. This is due to the impervious enclosure of the testing sheet and the colorimetric assay reaction pads, the inlet hole closing member which, upon swelling of the swelling component, closes the inlet hole, and the impervious barrier network.

Advantageously, the colorimetric assay reaction pads are placed onto the testing sheet. This can for instance be performed by means of a glue/adhesive.

The testing sheet may advantageously be made of a chromatograph filter paper.

In an embodiment of the present invention, the inlet section is centrally arranged with respect to body fluid channels branching out from the inlet section. The inlet hole then constitutes a body fluid entrance channel directed at least partly crosswise to the plane of the testing sheet. Hence, the body fluid arrives at the inlet section of the testing sheet, where the channels branch out, without moving through the testing sheet first. This makes space for more body fluid channels and assay reaction pads.

The swelling component is configured to swell when exposed to a liquid. The swelling component can comprise a body fluid absorbing polymer, the swelling of which being due to absorption of body fluid.

As the skilled person will appreciate, the term body fluid, as used herein, relates to a liquid.

The body fluid channels can in some embodiments be arranged in a fan-shaped configuration, directed radially out from a centered inlet.

Advantageously, the screening device according to the invention may comprise a reference absorption marker pad.

The on-diaper body fluid screening device may comprise at least ten colorimetric assay reaction pads, which are all configured to react to different biomarkers.

At least two body fluid channels can extend out from the position of the inlet section in oppositely, parallel directions.

Together with the on-diaper body fluid screening device, there may be a portable readout device comprising a camera, wherein the camera has a computer interface connectable to a computer.

Such a combination may further comprise a computer with computer readable software which, when executed, is configured to analyze colors of the colorimetric assay reaction pads, thereby analyzing the body fluid.

The camera, software and computer can advantageously be incorporated in a smartphone.

As discussed above, the invention relates to an on-diaper screening device, configured to collect body fluid and to detect a number of health biochemical parameters from a single body fluid sample. The on-diaper screening device according to the invention can comprise an arrangement of five main device sheets, including:
   a surface sheet through where the sample passes through while the sheet is kept dried;
   a collection sheet by means of which the sample is conducted to entering the testing sheet at downstream;

a testing sheet where the sample flows and contacts insulated assay-reaction pads;

a protection sheet serving as the barrier to avoiding sample splitting in the testing sheet at upstream;

a readout sheet allowing the display of the assay results as color changes occurred on the assay reaction pads.

The set of five device sheets can be sealed by placing the surface sheet and collection sheet on top of the testing sheet, which is covered by the protection sheet and readout sheet at the bottom. Around the inlet of the device is arranged the "self-locking" system for controlling sample entering to the testing sheet.

Sample collection and test are both conducted by the proposed device and method. Furthermore, the invention presents unique advantages of: handling small sample volumes when comparing with the conventional dipsticks; distributing the body fluid sample into multiple spatially-segregated regions to enable multiple assays to be performed simultaneously (or replicates of an assay) in a single device; detecting over tens of health parameters on diaper from a single body fluid sample; preventing cross-talking between the different reaction pads, and maintaining the reliability of the result for a period over 8 hours.

To overcome the shortcomings of existing "on-diaper" methods and conventional body fluid detection dipsticks, this invention provides a solution for a wide screening of body fluid parameters. The solution is suited for qualitative or semi-quantitative detection of more than ten body fluid markers. Considering the wide use of diapers in young and elderly persons, the solution enables collection of part of the body fluid and proceeds with automatic multiple-biomarker detection in one device.

A simple solution applied to diapers for detecting a wide range of biomarkers is imperative to detect important diseases, without a painful/time consuming sample collecting process. Thus, in this invention, the device is placed onto an unused diaper to reach the goal of collecting sufficient body fluid sample. Once the sample reaches the diaper, part of body fluid is collected and analyzed by the device. When the diaper is removed from the patient, the result of the multiple-biomarker analysis can be read through the transparent bottom sheet of this device after being placed out from the diaper. The analysis result will not suffer interference or loose the feasibility for typically at least 8 hours, which is typically the maximum time period between diaper changes for a patient wearing a disposable diaper. Remarkably, the solution shows preference to be incorporated to a disposable napkin, which is attached onto the diaper. For result readout, the napkin incorporating the device can be detached from the supporting diaper, and accurate colorimetric analysis can be conducted by a smartphone application.

EXAMPLE OF EMBODIMENT

The following description is made with reference to the appending figures, of which FIG. 1 is a schematic illustration of a three-dimensional "on-diaper" screening device realized by aligning and stacking a surface sheet, a hydrophobic collection sheet and a hydrophobic protection sheet, one patterned testing sheet and one transparent readout sheet;

Figure 4:
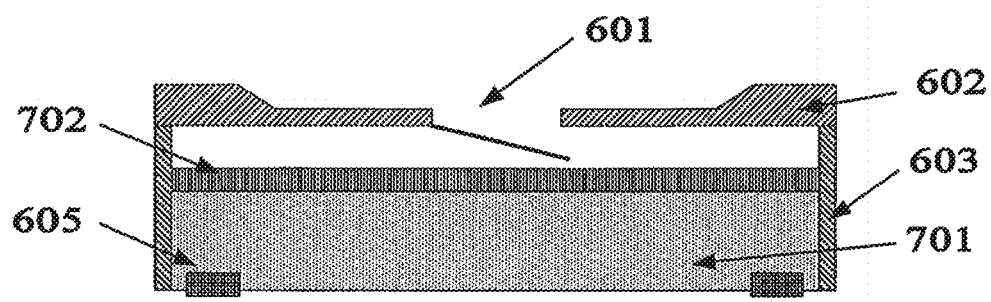
Figure 5:
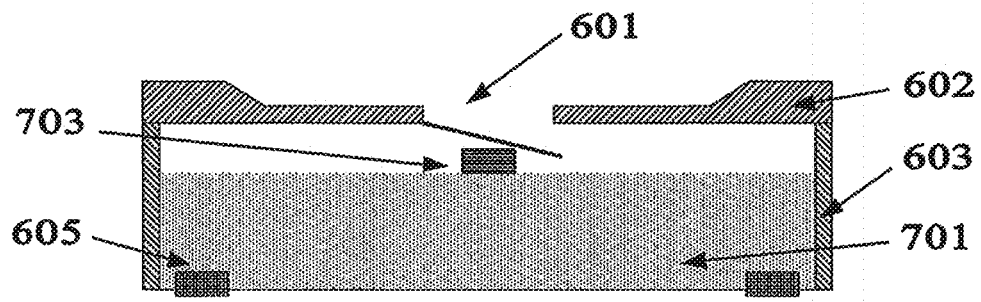
Figure 6:
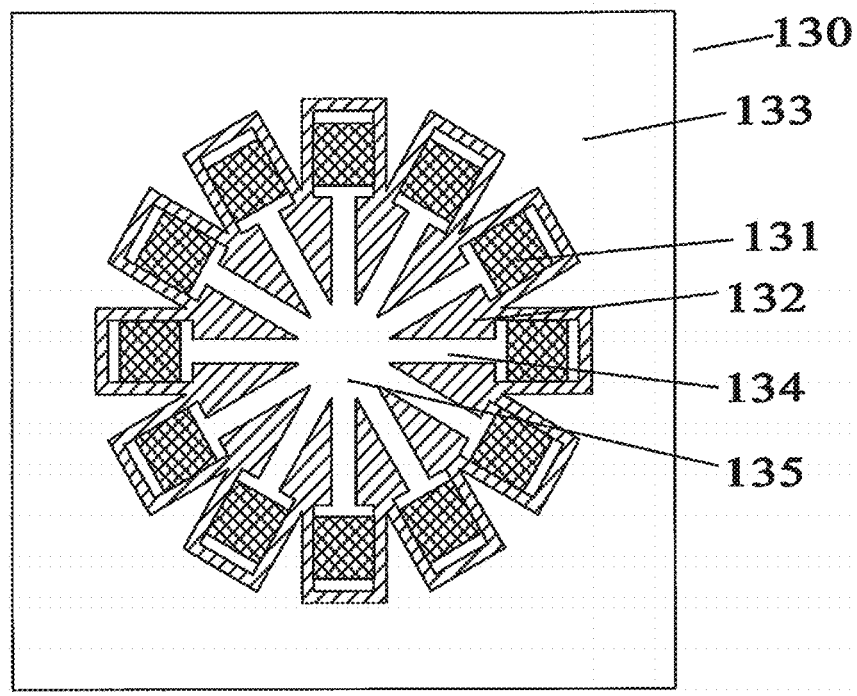
Figure 7:
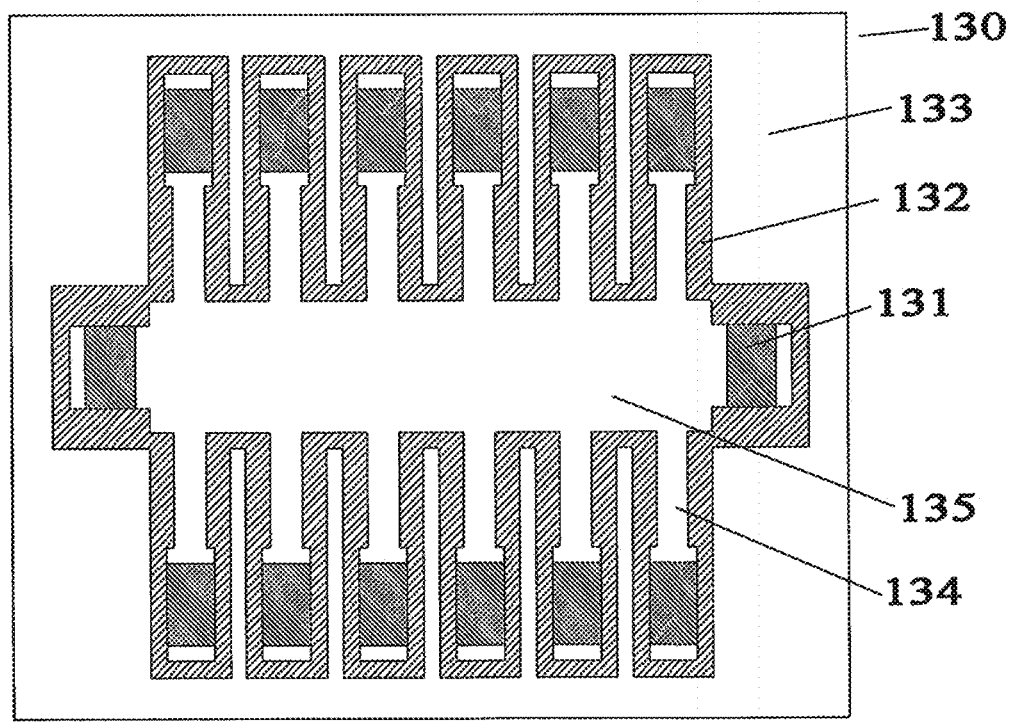
Figure 8:
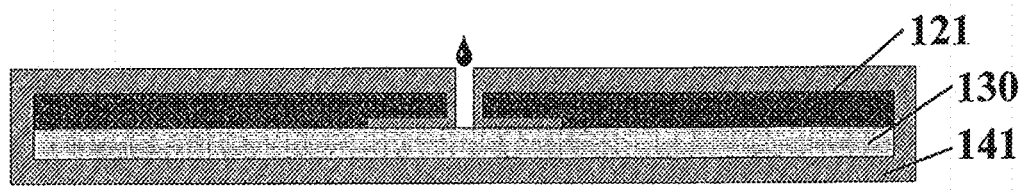
Figure 9:
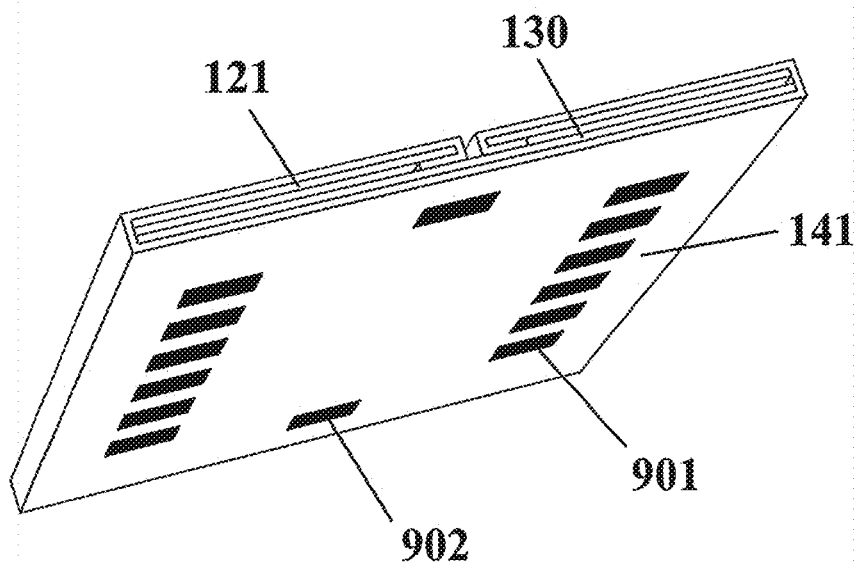
Figure 10:
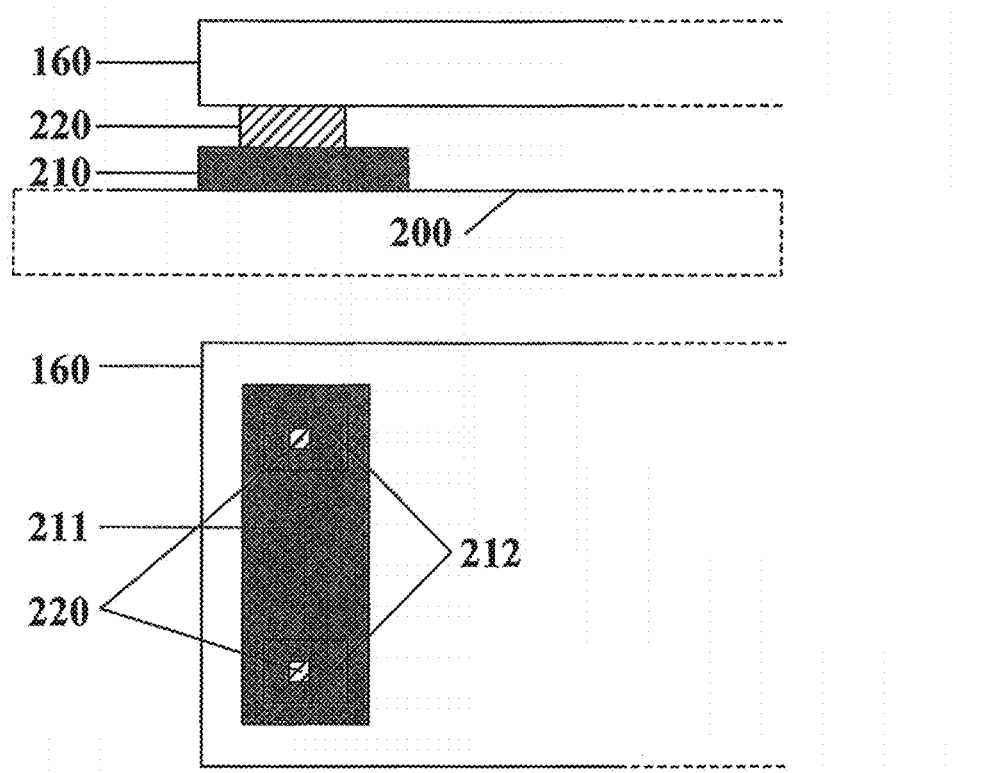
Figure 11:
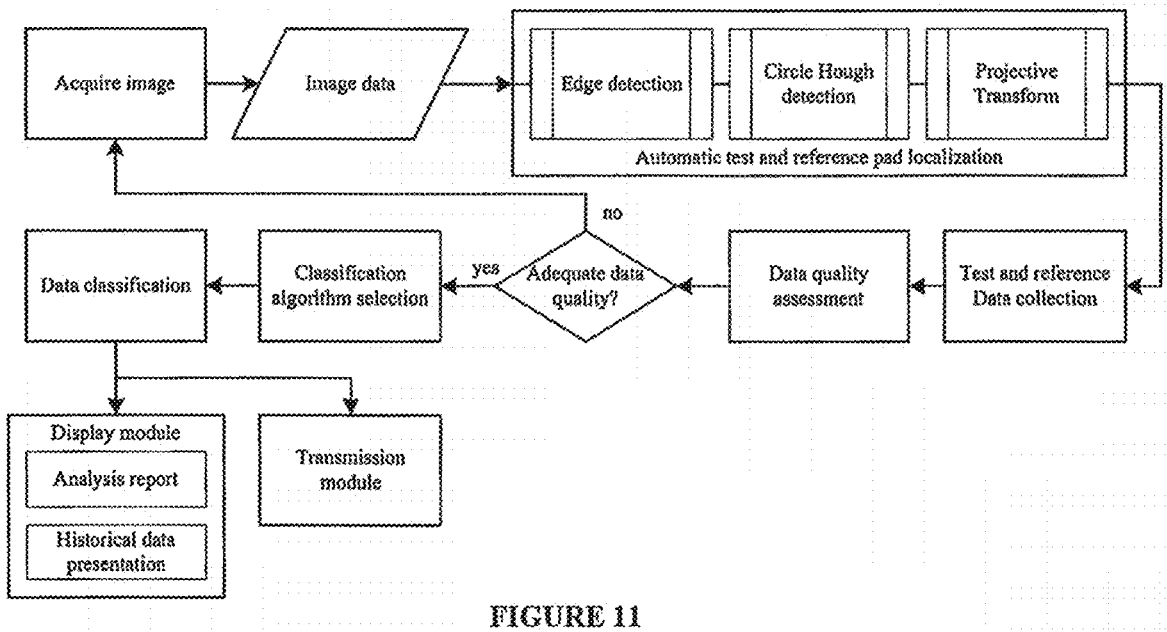
Figure 12:
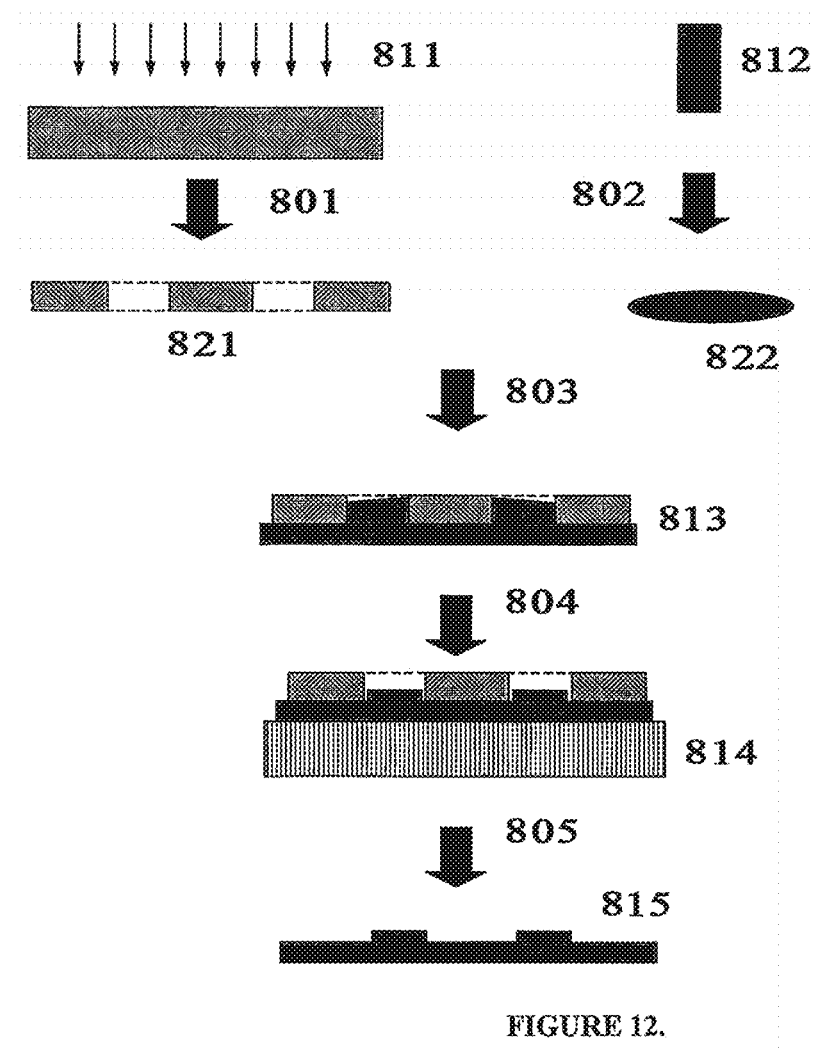

FIG. 4 incorporates the illustration of two examples of configuration for controlling body fluid sample entering the testing sheet with or without the additional swelling, highly porous layer added on top of the testing sheet. The layout depicted in FIG. 4 comprises a flexible valve arranged in the collection sheet and the porous testing sheet containing the assay reaction pads and containing swelling components in case of realizing one of the two examples;

FIG. 5 illustrates a third example of configuration for controlling the sample entering the testing sheet, comprising a flexible valve and a swelling material placed on top of the testing sheet containing the assay reaction pads;

FIG. 6 depicts a first example of configuration for the assay reaction pads, which are attached onto the testing sheet, and arranged in circle or a fan-shaped configuration, and isolated from each other by impregnated fluid-impervious barriers;

FIG. 7 depicts a second example of configuration for the assay reaction pads onto the testing sheet impregnated with the fluid-impervious barriers, which are arranged in series and in parallel to each other;

FIG. 8 is a cross-section, two-dimensional view of the assembled collection sheet, testing sheet, protection sheet and valve layer for the second example of configuration for the assay reaction pads onto the wax-impregnated filter paper;

FIG. 9 is a perspective view of the assembled collection, reaction, valve and protection layers for the second example of configuration for the assay reaction pads prepared onto the testing sheet impregnated with fluid-impervious barriers;

FIG. 10 illustrates a method of fastening the screening device onto the absorbent article using either a direct fastening mechanism, or a using an absorbent article fastening layer to which the screening device is attached;

FIG. 11 is a flow chart representing the algorithm used to analyze the colorimetric results of the test card; and FIG. 12 illustrates a preferable embodiment of deposition processes for patterning the testing sheet with wax-based fluid impervious barriers, which involves steps of mold printing, wax-solvent dissolution, wax printing onto chromatograph filter paper and solvent evaporation.

Figure 1:
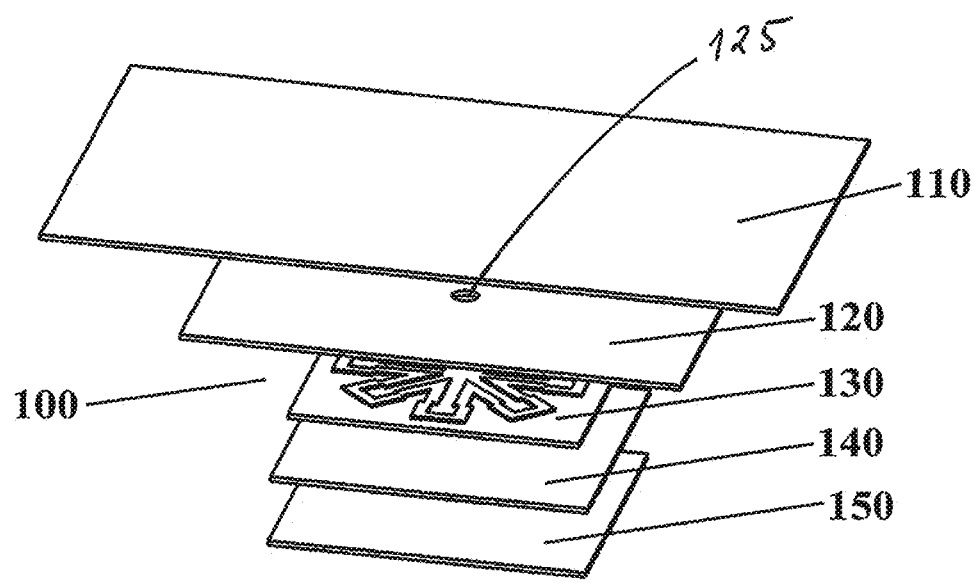

The "on-diaper" screening device 100 according to the invention, shown in FIG. 1, comprises the following main device sheets: surface sheet 110, collection sheet 120, testing sheet 130, protection sheet 140, and readout sheet 150. The working principle of the screening device 100 shall be described as following: firstly, the body fluid sample reaches the surface sheet 110. Within seconds, the sample passes the surface sheet 110 and reaches the collection sheet 120. In the collection sheet 120, the presence of a fluid-impervious barrier with shape-angular effect allows the body fluid sample to enter the centered inlet hole 125 of the collection sheet 120, which connects to the center of the testing sheet 130.

Figure 2:
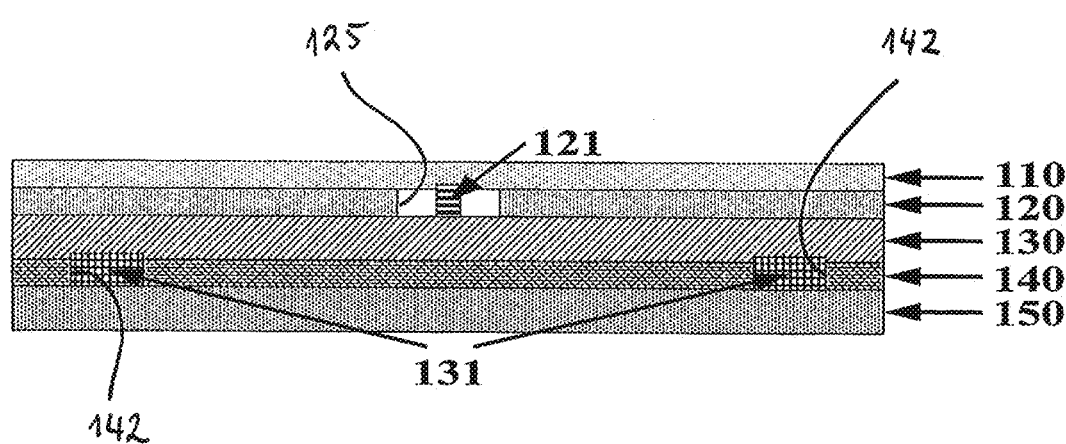
FIG. 2 is a cross-section view of the assembled on-diaper screening device, in which the surface sheet, the hydrophobic collection sheet, the hydrophobic protection sheet, and the patterned testing sheet are integrated with the active reaction areas, the transparent readout sheet and a sample flow control component.

Hereafter, the body fluid sample is driven across a porous medium until reaching a plurality of assay reaction pads 131, shown in FIG. 2. Here, the sample is absorbed by the assay reaction pads 131, which comprise assay regions. The fluid sample reacts with the chemicals embedded in the assay reaction pads 131. Some time, for instance tens to hundreds of seconds, after the first body fluid sample reaches the testing sheet 130, the centered inlet hole 125 of the collection sheet 120 is automatically closed to prevent a possible second body fluid sample from entering the testing sheet 130. From eight hours after the device is applied to the diaper (preferably through the use of a disposable napkin), the assay result can be seen through the protection sheet 140 and the readout sheet 150.

The surface sheet 110 of the on-diaper screening device 100 is preferably sterile hot air or made of hot-rolled, non-woven fabric materials. The surface sheet 110 contacts the skin of the diaper-wearing individual and is permeable to the body fluid. Good spatial structure of the surface sheet 110 increases the gap between its fibers. The surface sheet 110 absorbs the body fluid at a fast rate, and reduces the amount of re-wet fluid as a barrier to prevent the fluid back permeability. Meanwhile, it confers comfort and softness to the skin of the diaper wearing individuals.

Figure 3:
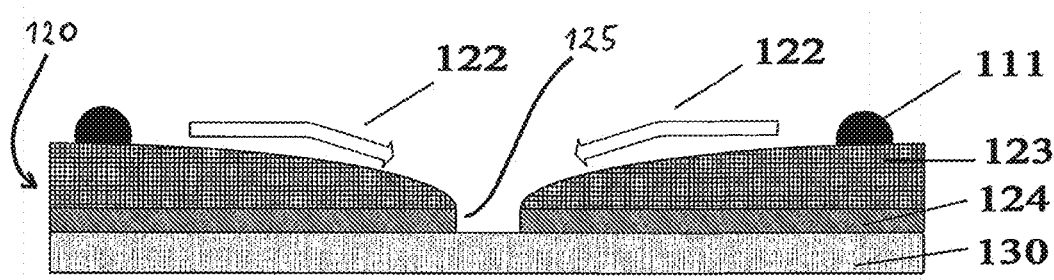
FIG. 3 is a cross-section view of a collection sheet comprising a hydrophobic structure with a thickness-variable, fluid-impervious layer prepared onto a hydrophobic surface.

The collection sheet 120 has a single inlet hole 125 arranged below the surface sheet 110, as also shown in FIG. 2. The collection sheet 120 is capable of gathering the body fluid and driving it to the entrance of the testing sheet 130, the entrance advantageously facing the inlet hole 125 of the collection sheet 120. The surface 124 of the collection sheet 120, cf. FIG. 3, contacting the testing sheet 130 is preferably made of hydrophobic materials. For instance, the collection sheet surface 124 can be made of non-woven fabric materials or silicone paper. The sheet structure of the collection sheet 120 is completed by adding an enhanced fluid-impervious layer 123 on top of the surface 124, with a thickness that gradually decreases from the edges of the screening device 100 towards the centered inlet hole 125. The fluid-impervious layer 123 is preferably impregnated on the collection sheet surface 124, and is preferably made of hydrophobic coating. As schematically shown in FIG. 3, droplets 111 of absorbed body fluid slide down along the shown arrows 122 through the fluid impervious layer 123, until reaching the centered inlet hole 125 and entering the testing sheet 130.

The testing sheet 130 is advantageously composed of absorbing porous media incorporating active areas for the detection of multiple biomarkers present in body fluid. Preferably, the porous sheet may be a chromatograph filter paper, and the assay regions are formed by attaching the assay reaction pads 131 onto the testing sheet 130. Such attachment can for instance be done by means of glue. The chemical adhesives used to fix the assay reaction pads 131 on the porous sheet must be chemically inert with respect to biomarkers.

The samples of body fluid reaching the centered inlet hole 125 from the collection sheet 120 segregate to the different active areas via absorbing porous media flow. To obtain an optimal absorbing rate, the porous sheet chosen or filter paper chosen, should have a proper aspect ratio for the porous media flow.

The assay reaction pads 131 containing the assay regions incorporate chemical substances or reagents that specifically interact with the biomarkers present in body fluid. Preferably, the assay reaction pads 131 can specifically target but not limited to glucose, ketones, specific gravity, blood, pH, proteins, bilirubin, urobilinogen, creatinine, nitrite, leukocytes. Other non-traditional biomarkers signaling the presence of infectious bacteria, such as but not limited to xanthine oxidase, trimethylamine, myeloperoxidase, and acetic acid can be detectable. The accuracy of detecting these non-traditional biomarkers by the screening device 100 is not affected by contamination from the surrounding environment. The layout of the assay reaction pads 131 of the testing sheet 130 is intended to be independent of the desired biomarkers, and should therefore be changeable according to the requirements set by the clinical application.

Surrounding the centered inlet hole 125 there is a valve arrangement 121, here in the form of a valve layer 121, that provides On/Off control of sample entering the testing sheet 130. The valve mechanism involves flexible switches and/or swelling components to seal the inlet of the screening device 100, thus preventing passage of a possible second body fluid sample onto the testing sheet 130.

Examples of realizing the valve layer 121 are depicted in FIGS. 4 and 5. The generalized principle can be described as following. After the body fluid sample enters the inlet hole 125, it faces sets of transportation paths with different terminal location. One set of transportation paths goes from the inlet hole 125 to the assay reaction pads 131 on the testing sheet 130. Another set of parallel-arranged transportation paths goes from inlet hole 125 to the valve layer 121. Transportation paths to valve layer 121 can also be arranged in series, although it is likely less effective than parallel-arrangement. Series arrangement involves arranging the transportation path to the valve layer 121 after the assay reaction pads 131, which makes the valve layer 121 the only terminal location.

While the body fluids are transported throughout the screening device 100, the material composition, material parameters, and device design parameters will affect the proportion of body fluid ending up at the different terminal locations. Tunable overall function parameters for successful operation is (but not limited to): (a) the resistance exerted by transportation paths on the body fluid through design of the physical dimensions of transportation path geometry, and diffusivity of transportation path material; (b) the driving force is a potential difference generated by termination material absorption, which is the assay reaction pads 131 in the testing sheet 130 and sealing material in the valve layer 121; (c) dimensions and material parameters of the sealing material related to expansion due to absorption.

The successful operation of the valve layer 121 requires tuning of parameters in such a way that a sufficient amount of fluid is capable of reaching the assay reaction pads 131 before the valve layer 121 seals the inlet. Also demandingly, the successful operation of the valve layer 121 requires tuning of the parameters in such a way that a sufficient amount of fluid arrives to the valve layer 121 so that the valve layer 121 closes completely in a finite time.

In the testing sheet 130, the assay reaction pads 131 shall be isolated from each other to prevent cross-talking of the generated colorimetric test results. The specific reactions occurring in the assay regions of the testing sheet 130 generate color changes on the arranged assay reaction pads 131, and cross-talking of the generated colors typically occurs in the conventional dipsticks. The screening device 100 according to the present invention solves the challenge of cross-talking by segregating the assay reaction pads 131 using fluid-impervious barriers, preferably made of hydrophobic materials patterned onto the porous, planar sheet. These barriers allow the creation of two-dimensional fluid flow paths or hydrophilic channels onto the porous sheet. Within these channels, the body fluid sample is transported via an absorbing porous medium flow towards the assay reaction pads 131. The barriers shall guarantee the non-communication of fluid between two hydrophilic areas separated or isolated by hydrophobic coating materials such as, but not limited to, non-reacting wax, nanoparticles, hydrophobic polymers or composites. The dimensions, such as effective length, width and thickness of the generated hydrophilic channels, shall be designed according to liquid permeating flow based on Darcy's law, so as to optimize the proportion of body fluid sample absorbed by the reaction pads, especially in the cases of relatively small volumes of body fluid are presented. Relatively small volumes, here, refer to sample volumes close to the maximum amount of absorbable volume in the preferred embodiment of the device. Thus, in this context, to verify delivery of sufficient body fluid sample to the entire testing areas, one or two reference absorption markers can in addition be assessed using two additional pads attached onto the testing sheet. This procedure helps to determine whether the body fluid reaches all assay reaction pads or not.

To isolate or segregate the multiple assay reaction pads 131 onto the same testing sheet 130 and create the corresponding hydrophilic channels, a fluid-impervious barrier network 132 is realized onto the testing sheet 130. Two preferable embodiments of the fluid-impervious barrier network 132 are disclosed. The first embodiment, as depicted in FIG. 6, involves a circular arrangement of the assay reaction pads 131 with the same radial distance to the center of the testing sheet 130. Another embodiment, depicted in FIG. 7, involves a series and parallel arrangement of the assay reaction pads 131 with generated hydrophilic channels mirrored to each other two by two. These two designs take into account the equal and most possibilities of obtaining the body fluid sample.

The testing sheet 130 is covered at the bottom side by the protection sheet 140. This protection sheet 140 is preferably made of either non-woven fabric materials or even silicone paper with enhanced hydrophobicity. The protection sheet 140 confers protection to the testing sheet 130 by preventing excess wetting of the hydrophobic fluid-impervious barriers in the testing sheet 130, which may lead them to collapse, and avoiding contact of the wet testing sheet 130 with the transparent readout sheet 150. Overall, the protection sheet 140 is to ensure that the absorbed body fluid does not spread out from the hydrophobic barriers, and thus the absorbed body fluid is confined to the hydrophilic channels and assay reaction pads 131 of the testing sheet 130. Excessive wetting of the absorbing porous medium composing the testing sheet 130 shall preferably be avoided to maintain the robustness of the screening device 100.

In one of the preferred embodiments, the protection sheet 140 in individual connection with the collection sheet 120 covers the testing sheet 130, as it shows in FIGS. 1 and 2. In this case, the protection sheet 140 and the collection sheet 120 can be made of different fluid-impervious or hydrophobic materials. Moreover, a larger fluid-impervious sheet can be arranged by combining both the protection sheet 140 and the collection sheet 120 if made of same material. This combined large surface can wrap up the testing sheet 130, thus conferring enhanced compactness to the setting without compromising the function. This another preferred embodiment of the invention is shown in FIGS. 8 and 9. The wrapping structure also covers the valve layer 121 and is "sandwiched" between the surface sheet 110 and transparent readout sheet 150.

The protection sheet 140 is covered at its bottom side by the transparent readout sheet 150 that allows the colorimetric test results to be visually observed or ready for analysis by a smartphone application. Preferably, the readout sheet 150 is made of, but not limited to transparent polyethylene terephthalate or other transparent non-permeable plastics. Moreover, the readout sheet 150 shall not allow permeation of air and humidity into the screening device 100 and contact with the assay reaction pads 131. Also preferably, an air gap should be left between the readout sheet 150 and the protection sheet 140 and/or a nylon film mesh can be added to the bottom side of the protection sheet 140, and thus covering the assay reaction pads 131. The air gap and use of nylon film mesh enhances the non-interference of the colorimetric test results and contributes to maintain the wetting of the pads, which is necessary to maintain the accuracy of the colorimetric test results for over 8 hours.

Furthermore, it is preferred that the transparent readout sheet 150 comprises an external diffuse reflection coating that minimizes the effect of specular reflected light, for accurate analysis of the colorimetric results. How to effectively, or to the greatest extent, avoid the reflected light affecting on the result analysis shall be taken into consideration, not only in the structural design, but also in the smartphone application analysis.

The setting formed by the stacked sheets 110, 120, 130, 140, 150 is preferably added into a testing card and/or being part of a disposable napkin, to be placed on a diaper. Preferably, the stacked sheets 110, 120, 130, 140 and 150 are attached together by use of conventional bonding techniques, including but not limited to thermal bonding, pressure-sensitive adhesives or chemical adhesives non-reacting with biomarkers present in sample and non-reacting with compounds immobilized within the assay reaction pads 131.

The testing card and/or the parts of the disposable napkin in which the stacked setting is integrated shall be hermetically sealed with the centered inlet hole 125 coming into contact with the exterior environment through the surface sheet 110. Preferably, for some embodiments of the screening device according to the invention, the hermetic sealing shall contribute to preserve the long-term wetting of the assay reaction pads 131 and to avoid reagent/product evaporation from the assay reaction pads 131. These features are of priority importance for guaranteeing the validity of the colorimetric test results for over 8 hours.

The testing card and/or the parts of the disposable napkin containing the screening device 100 shall be suitable for reversible attachment to an absorbent article and/or diaper contacting the body fluid sample. The reversible attachment is preferably achieved by use of physical fastening components, such as mechanical hook- and/or loop-like fasteners, bur inspired hooks, bandage wrap clips, small plastic barbs or miniaturized pins penetrating the surface of absorbent article and/or diaper and fastening. On the contrary to standard chemical adhesion or gluing, the use of mechanical fasteners allow easy re-position of the device onto the absorbent article and/or diaper in case of misplacement, thus reducing the occurrence of invalid tests. In preferred embodiments of device and method, the mechanical fastening 220 can involve placement of fastening pads 210 as corner pads 212 or as fastening strips 212, onto the absorbent article and/or diaper 200, as represented in FIG. 10, before attaching the testing card and/or the testing napkin 160. For ensuring device fixing onto absorbent article and/or diaper, one pair of fastening pads, at least, per device can be added.

In preferred embodiments of the "on-diaper" screening device and method, the colorimetric test results produced on the assay reaction pads 131 are either ready for direct visual observation and/or ready for analysis by a smartphone application. The smartphone application preferably compatible to Android and IOS systems encompasses but not limited to the following modules: image capture module; lens distortion correction module; perspective correction module; data sampling module; classification module; display module; communication module. The methodology behind the smartphone application is summarized in FIG.

11. Briefly put, the smartphone app accesses the camera of the smartphone to obtain photographs of the results displayed on the assay reaction pads. The acquired photographs, saved in but not limited to JPEG (Joint Photographic Experts Group) or DNG (digital negative, or other type of raw file) image formats, are subjected to image correction algorithms, that eliminate errors inherent to smartphone camera, errors associated with position of the photographers relative to illumination sources, errors from variation in, but not limited to, illumination color and illumination intensity, errors from variation in adjustable and automatic camera settings, and errors from uncontrollable automatic file processing in formats such as JPEG. Further, the object of analysis is subjected to algorithms of transformation, calibration and testing that includes, but is not limited to, automatic collection of data from the object of analysis through pattern recognition algorithms and multivariate statistics classification algorithms such as canonical, linear and quadratic discriminant analysis, and multivariate regression analysis. The graphical display allows access to the analysis report showing qualitative readings (negative−; positive+) or semi-quantitative readings (negative−; positive+; positive++; positive+++; etc.) and quantitative detection (such as but not limited to concentration) results for the multiple biomarkers present in body fluids sampled from absorbent article 200. Preferably, the display module presents graphs of historical data showing the variation of biomarkers as analyses are performed over time. The communication module preferably allows sending of emails to physicians and/or health care providers with the attached urinalysis report, and allows wireless (e.g. Bluetooth) communication with center databases in hospital and/or other health care providing institutions.

The beneficial effects of the present invention: compared with conventional body fluid strips, the screening device according to the invention shows a compact, convenient and easy-to-operate solution for "on-diaper" screening of multiple biomarkers of important diseases; the integrated setting of the screening device 100 and related method allow not only real-time collection of body fluid sample but also proceed with detection and analysis; the invention presents a simple device with no incorporated electronics and made of economical and/or recyclable materials that has multi-detection function with no need for special equipment, thus effectively reducing the workload of detection process and improving overall detection efficiency; the architecture of the screening device 100 reduces the required volume of body fluid for testing, thus effectively solves the difficulty of collecting body fluid sample from elderly patients; the "on-diaper" device eliminates the process of sample transfer to laboratory centers, thus reducing the risk of sample contamination; the invention gathers a number of reagent reaction pads in one "on-diaper" device to determine the patient's health status; the result of colorimetric reactions advantageously lasts for over 8 hours with no interference of cross-talking between reaction pads; the "on-diaper" screening method may comprise a smartphone application that complements the human-eye observation, and allows accurate analysis of the colorimetric test results saving data for further disease diagnosis.

The on-diaper screening device according to the present invention offers five basic features to solve current diagnosis challenges: (i) compatibility with small volumes of sample which is essential when sample size is limited, and samples are difficult to obtain; (ii) maintaining the result of assay reaction result for over 8 hours; (iii) guaranteeing device isolation (centered inlet sealing) after one body fluid sample enters the device; (iv) incorporation of pads targeting body fluid biomarkers that are resistant to the exterior contamination; (iv) distribution of the body fluid sample into multiple spatially-segregated regions to enable multiple assays performed simultaneously on a single device.

In the following, some non-limiting examples of embodiment of the present invention is given.

Example 1—Cases of Self-Locking Mechanisms

The sealing or isolation of the centered inlet hole 125 of the screening device 100, after entering of the body fluid sample, is necessary to ensure non-interference from possible second body fluid samples and exterior contamination.

The present cases show preferred solutions for realizing the valve layer 121 or valve arrangement 121 depicted in FIG. 2. The embodiments can encompass a flexible switch 601 attached or being part of the collection sheet 602, and swelling components 702 and 703 that are arranged on top of a filter paper 701 (i.e. the testing sheet 130). Before arranging the collection sheet 602, and the swelling component 702, 703 onto the filter paper 701, the filter paper 701 is impregnated with hydrophobic wax, used as the fluid impervious barriers 603 (barrier network 132) in this preferred solution. The material for the flexible switch 601 may be the same as that of the bottom face of the collection sheet 602.

The first case of "self-locking" mechanism is presented with reference to FIG. 4. FIG. 4 illustrates a swelling component 702, but for the discussion of this embodiment, the shown swelling component 702 is imagined not to be present. Here, the sealing of the flexible switch 601 shall be ensured by expansion of the filter paper 701 due to absorption of the body fluid. This can take place either by swelling components that modify the filter paper 701 or by accessory chemical reactions occurring in the modified filter paper 701 and which are different than those colorimetric reactions occurring in the assay reaction pads 605 (cf. assay reaction pads 131). Sealing by means of the flexible switch 601 shall be completed within seconds or few minutes after the assay reaction pads 605, which are segregated by the wax barriers 603, have been fully wetted with the body fluid sample.

In contrast to the above, a second embodiment of the "self-locking" mechanism comprises the swelling component 702 depicted in FIG. 4. Here, the sealing of the flexible switch 601 is conducted by expansion of the swelling component 702, which is a highly porous layer added on top of the filter paper 701 (i.e. the testing sheet 130). The pores of the swelling component 702 shall preferably be of micron dimensions. Expansion of the swelling component 702 is caused by absorption of small part of body fluid while most of it enters the filter paper. The porous layer of the swelling component 702 should have a great increase in dimension when the small part of body fluid enters and is absorbed by it. The complete sealing of the flexible switch 601 is achieved seconds or few minutes after a part of body fluid passes through the swelling component 702 and the assay reaction pads 605 (cf. assay reaction pads 131), which are segregated by the wax barriers 603, are then fully wetted with body fluid sample.

The third case of "self-locking" mechanism is represented in FIG. 5. In this embodiment, the sealing of the flexible switch 601 is conducted by expansion of a swelling block 703 added on the top of the filter paper 701. Preferably, the swelling block 703 is made of a hydrogel-based material, and may incorporate silver nanoparticles for enhancing inhibition of bacteria growth. Expansion of the swelling block 703 is caused by swelling due to a small part of body fluid, while most of the body fluid enters the filter paper. The complete sealing of the flexible switch 601 occurs seconds or few minutes after the assay reaction pads 605, segregated by the wax barriers 603, are fully wetted with the body fluid sample.

Example 2—Cases of Pads and Wax Network Arrangement

In preferred embodiments of the invention, surrounding the centered inlet section 135 (cf. FIG. 6 and FIG. 7) of the testing sheet 130 is arranged the wax barrier network 132, that encloses the assay reaction pads 131 attached onto the filter paper 133. The use of wax printing techniques confers flexibility to the design of the wax barrier networks onto the testing sheet 130. Two embodiments of wax network design that have effects on the display of the test results are described.

The first preferred embodiment of pad and wax network arrangement is represented in FIG. 6. Here, hydrophilic channels 134 formed by the wax barriers are arranged as radius of a circle with the inlet 135 as the center. That is, the hydrophilic channels 134 form a fan-shaped configuration about the centered inlet 135. This arrangement enables equal and simultaneous distribution of absorbing body fluid sample towards the different assay reaction pads 131. The example depicted in FIG. 6 ensures the integration of twelve assay reaction pads targeting twelve different biomarkers possibly present in body fluid sample. The assay reaction pads 131 are centered within rectangular-shape active areas on the testing sheet 130. The portions of filter paper 701 (FIG. 4 and FIG. 5) left between the assay reaction pad and the wax wall enhance wetting of the assay reaction pads 131 to extend the color retention period of the pads. The testing sheet 130 comprises the filter paper 701.

The second preferred embodiment of assay reaction pad and wax network (i.e. barrier network 132) arrangement is represented in FIG. 7. Here, the hydrophilic channels 134 formed by the wax barriers 132 are arranged in parallel, and each of the assay reaction pads 131 faces to the corresponding one. In this case, a wider inlet section 135 for the testing sheet 130 and different numbers of circle holes (inlet holes 125) in collection sheet 120 are designed to ensure distribution of body fluid sample among the different assay reaction pads 131 and to ensure their complete wetting for the colorimetric testing. Although the existing probability of simultaneous distribution of body fluid among the pads by the absorbing porous medium flow is not high with this wax network arrangement, the filter paper 133 complements with a high wettability rate to guarantee rapid sample flow through the porous medium. Especially, this case of pad and wax network arrangement confers better alignment of the assay reaction pads 131 and allows easy colorimetric result visualization and interpretation. The example depicted in FIG. 7 ensures the integration of fourteen assay reaction pads 131, of which twelve are testing pads targeting twelve different biomarkers and two remaining pads function as reference markers of paper wetting. Thus, the two reference pads will display a positive result if all the other twelve pads are entirely wetted.

Example 3—Cases of Hydrophobic Barriers

The fluid impervious barriers impregnated on the filter papers can effectively prevent cross-talking between the different assay reaction pads 131 on the testing sheet 130, and enhance the color retention period of the pads. In example cases of fabrication, non-reacting wax is used for the hydrophobic, fluid-impervious barriers. An example of fabrication method for realizing the hydrophobic wax barriers, is described with reference to FIG. 12.

Impregnation of hydrophobic wax, such as but not limited to bee wax, on the filter paper can preferably be conducted by either dipping or screen printing processes. The wax dipping involves the use of a mold dipping into melted wax to transfer a pattern to the filter paper. The wax barriers are formed onto the paper after short-time paper baking. Although the practicability of the wax dipping processes, the regularity of the formed channels onto the same filter paper are often difficult to control. Thus, to achieve higher uniformity of the wax barriers, the wax screen printing process, summarized in FIG. 12, is preferably used to impregnate the wax on the chromatograph filter paper. This technique involves steps of mold printing 801, wax rubbing 802, wax printing 803, baking 804 and formation of the wax channels 805. As depicted in FIG. 12, high-resolution laser engraving 811 is used to fabricate the mold 821 while chemical solvents are applied to solid wax block 812 making it rubbed 822. After proper cleaning, the screen mold is placed onto the filter paper and the rubbed wax is printed onto this setting 813. The setting 813 is placed in or onto a hot source 814, preferably a hot plate or baking oven, to allow the chemical solvents to evaporate and the wax to melt and diffuse into the filter paper. After the baking time and removal of the setting 813 from the hot source 814, the hydrophobic wax barrier network 132 is formed on the porous medium filter 815 (cf. testing sheet 130, filter paper 701).

Example 4—Cases of Sheet Packaging Arrangement

The pad and wax network arrangement depicted in FIG. 7 may lead to a different embodiment of stacking the collection sheet 120, valve layer 121, testing sheet 130 and protection sheet 140, when comparing to the layout shown in FIG. 2. FIG. 8 and FIG. 9 show another preferred embodiment for "sandwiching" the testing sheet 130. Herein, the collection sheet 120 and protection sheet 140 are combined into one wrapping structure 141 and made of same hydrophobic material. Besides the testing sheet 130, the wrapping structure 141 also encloses the valve layer 121. The valve layer 121 is divided into two separate sub-layers and placed besides the centered inlet 135 (cf. FIG. 7) of the screening device 100.

Each sub-layer of the valve layer 121 is preferably made of two pieces of a hydrophilic permeable material that incorporates swelling polymer beads in the portions of material surrounding the centered inlet 135. The two pieces of hydrophilic permeable material can be but not limited to hot-rolled, non-woven fabric as for the surface sheet 110, and the two pieces of sub-layer can for instance be bonded tightly by thermal bonding. Same procedure of thermal bonding can be used for attaching the surface sheet 110 to the readout sheet 150.

In the embodiment of sheet packaging arrangement shown in FIGS. 8 and 9, when the body fluid sample reaches the inlet section 135 (FIG. 7), a small volume of body fluid sample passes through the hydrophilic permeable material and is absorbed by the enclosed polymer beads. Swelling of beads at both sub-layers of the valve layer 121 leads to sealing and self-locking of the centered inlet hole 125. The success of the self-locking switch is dependent upon the quantity of swelling polymer beads within the valve sublayers and is dependent upon the gap width defining the centered inlet hole 125.

The wrapping structure 141 depicted in FIGS. 8 and 9 possesses rectangular- or square-shaped hole entrances 901, 902, whose dimensions match to those of the rectangular- or square-shaped assay reaction pads 131. The assay reaction pads glued on the reaction zones of the testing sheet 130 shall be aligned to the corresponding holes of the wrapping structure 141, and make sure that the testing sheet 130 does not move within the wrapping structures. The holes arranged at bottom side of the wrapping structure 141 allow display of the colorimetric test results from the testing pads 901 and from the reference pads 902. The aforementioned sheet packaging processes shall be conducted in clean and dried environment to avoid contamination and humidity effects especially to the assay reaction pads 131.

Example 5—Case of Smartphone Assisted Reading of Colorimetric Test Results

After testing and removal from the absorbent article or diaper, the screening device 100, incorporated in a testing card or being part of a disposable napkin, is placed with the colorimetric reaction pads facing upwards on a flat elevated surface such as a table. The person operating the smartphone camera stands next to the elevated surface, preferably in a well or normally lit area, while avoiding situations where there is one strong illumination source behind the operator, as this will cast shadows over the surface of the assay reaction pads 131, which will affect colors.

The person operating the smartphone camera focuses the image with the image capture module and makes sure all references and reaction pads are present in the image then takes a picture of the assay reaction pads and references.

If the recorded picture shows signs of lens distortion (straight lines being perceived as curved by the camera lens), this can be removed with the lens distortion correction module.

The smartphone camera angle of tilt in relation to the plane of the assay reaction pads, affects the perspective and the cameras perception of shape. For a rectangular-shaped device, the perceived shape is trapezoidal when the camera observation vector differs from being perpendicular to the reaction pad plane. The perspective is removed with the perspective correction module. To achieve user-friendliness, this process is automated. By placing alignment marks on the surface of the transparent readout sheet 150, a pattern recognition algorithm can automatically locate the position of corners, with subsequent removal of perspective.

After perspective correction, the image has fixed and known dimensions, and the relevant positions of the assay reaction pads and reference pads can be found through their physical locations (as defined in the designed) with the data sampling module. An equal number of pixels are sampled in each location.

The classification model uses statistical analysis such as, but not limited to, canonical correlation analysis or multivariate regression analysis to build a training model based on reference data which is used to classify the colors sampled from 131. The degree of success in constructing a good training model can affect whether the results are presented as qualitative, semi-quantitative or quantitative.

The display module presents the analyzed and classified data to the user. A display format that is useful in a context of reporting is a summary of all results in one test. A display format that is useful for long term reporting is the time dependence of biomarker results.

Examples of Various Embodiments

Below are some different embodiments and listing of various possible features that may be used with some possible embodiments of the screening device according to the invention.

(a) An on-diaper screening method and device for multi-parameter body fluid test, comprising: a hydrophilic, permeable medium in the form of a flexible porous sheet through which the body fluid sample passes through while the sheet is kept dry; a first hydrophobic sheet impregnated with a thickness-variable fluid impervious barrier, capable of gathering the body fluid sample and driving it to its centered inlet; an absorbing porous medium in the form of a flexible hydrophilic sheet impregnated with a pattern of fluid-impervious barriers that define the boundary of flow-path channel networks and that segregate multiple insulated assay reaction pads permanently attached to the sheet; a second hydrophobic sheet capable of preventing excessive wetting of the fluid-impervious barriers and ensuring confinement of the absorbed body fluid sample to the flow-path channel networks and assay reaction pads; a non-permeable transparent sheet, with an anti-specular-light reflection coating, through which are visible the colorimetric results generated from the assay reaction pads.

(b) An on-diaper screening device as claimed in (a) wherein said device sheets are arranged and sealed by placing said permeable, dry sheet and said hydrophobic sheet on top of said porous sheet impregnated with fluid-impervious barriers and assay reaction pads, which is covered at its bottom side by said second hydrophobic sheet and said non-permeable transparent sheet.

(c) An on-diaper screening method and device claimed in (a) wherein said sealed sheets are preferably incorporated into a testing card and/or being part of a disposable napkin, that attaches reversibly to an absorbent article and/or diaper by means of mechanical fastening that may or may not involve previous placement of fastening pads or fastening strips onto said absorbent article and/or diaper.

(d) An on-diaper screening device as claimed in (a) wherein said multiple insulated reaction pads are disposed in fluid communication with said flow-path channel networks surrounded by said fluid-impervious barriers, and the layout of pad and channel network arrangement is independent from targeted biomarkers present in said body fluid sample, and said layout is variable according to requirements set by the clinical application.

(e) An on-diaper screening method and device claimed in (a) wherein a flexible switch and/or valve, being part of said first hydrophobic sheet, seals the centered inlet of said device a moment after the body fluid sample reaches the assay reaction pads in where the sample is absorbed, and wherein said flexible switch and/or valve is sealed by expansion of swelling polymers and/or other compounds and/or swelling structures placed underneath, and wherein said on-diaper screening device possesses the ability of isolating the assay reaction areas from exterior contamination.

(f) An on-diaper screening device as claimed in (a) wherein said second hydrophobic sheet can either be placed separately from said first hydrophobic sheet or be combined with said first hydrophobic sheet to form a sole wrapping structure that encloses said porous sheet impregnated with fluid-impervious barriers and assay reaction pads, and wherein said wrapping structure encloses said flexible and/or valve which incorporates swelling polymer particles within two sealed permeable hydrophilic layers, and wherein said swelling particles causes sealing of said centered inlet when partially absorb body fluid sample.

(g) An on-diaper screening method and device claimed in (a) wherein said assay reaction pads incorporate chemical substances or reagents which alone or together provide visible color changes in the multiple pads corresponded specifically to clinically relevant concentrations of targeting biomarkers, which can be but limited to glucose, ketones, specific gravity, blood, pH, proteins, bilirubin, urobilinogen, creatinine, nitrite, vitamin C, leukocytes, and said visible color changes can either be observed by human eye or be digitized in an image acquired by a smartphone camera right after said device claimed in (a), as incorporated to said testing card and/or being part of a disposable napkin is mechanically detached from said absorbent article and/or diaper, and said clinically relevant concentrations corresponded to said color changes can be determined and analyzed by a smartphone image processing application.

(h) An on-diaper screening method and device wherein the assay reaction pads claimed in (g) incorporate chemical substances or reagents which alone or together reacts specifically with non-traditional biomarkers signaling the presence of infectious bacteria and resistant to exterior contamination, such as but not limited to myeloperoxidase, xanthine oxidase, acetic acid, and trimethylamine.

(i) An on-diaper screening method wherein the smartphone image processing application claimed in (g) is applied to the colorimetric results from said assay reaction pads of device claimed in (a), following detachment of said testing card and/or disposable napkin from said absorbent article and/or diaper, and wherein said smartphone application is compatible to either Android and/or IOS systems encompassing algorithm modules of image capture, lens distortion correction, perspective correction, data sampling, data transformation, calibration and testing, display and communication.

(j) An on-diaper screening method wherein the smartphone application claimed in (g) accesses the camera of the smartphone to acquire photographs of the colorimetric results obtain from device claimed in (a), and wherein said acquired photographs are subjected to image correction algorithms, eliminating errors inherent to camera, errors associated with operation, errors associated with illumination conditions, errors inherent to camera settings, errors associated with image file formats, and wherein the corrected image for analysis is subjected to pattern recognition algorithms and multivariate statistics classification algorithms for data transformation, calibration and testing, and wherein an analysis report is generated showing qualitative, semi-quantitative and quantitative detection results whose evolution over a period of time is displayed, and wherein said analysis report and results are communicated and accessible to physicians and/or health care providers.

The invention claimed is:

1. An on-diaper body fluid screening device comprising:
a surface sheet permeable to body fluid;
a collection sheet impervious to body fluid;
a testing sheet that is body fluid absorbent and provided with a plurality of colorimetric assay reaction pads;
a protection sheet impervious to body fluid and covering a bottom side of the testing sheet;
a transparent readout sheet through which the plurality of colorimetric assay reaction pads are visible;
wherein the protection sheet has formed therein a plurality of colorimetric assay-reaction pad-receiving openings;
wherein a number of the plurality of the colorimetric assay-reaction pad-receiving openings and a number of the plurality of colorimetric assay reaction pads are identical;
wherein the collection sheet comprises an inlet hole arranged over an inlet section; and
wherein a swelling component is arranged in association with the inlet hole and an inlet-hole closing member.

2. The on-diaper body fluid screening device according to claim 1, wherein the inlet section is centrally arranged with respect to body fluid channels branching out from the inlet section, wherein the inlet hole constitutes a body fluid entrance channel directed at least partly crosswise to the plane of the testing sheet.

3. The on-diaper body fluid screening device according to claim 1, wherein the swelling component comprises a body fluid absorbing polymer, the swelling of which being due to absorption of body fluid.

4. The on-diaper body fluid screening device according to claim 2, wherein the body fluid channels are arranged in a fan-shaped configuration, directed radially out from a centered inlet.

5. The on-diaper body fluid screening device according to claim 1, comprising a reference absorption marker pad.

6. The on-diaper body fluid screening device according to claim 1, wherein the colorimetric assay reaction pads comprise at least ten colorimetric assay reaction pads configured to react to different biomarkers.

7. The on-diaper body fluid screening device according to claim 1, wherein at least two body fluid channels extend out from the position of the inlet section in opposite parallel directions.

8. The on-diaper body fluid screening device according to claim 1, comprising a portable readout device comprising a camera comprising a computer interface connectable to a computer.

9. The on-diaper body fluid screening device according to claim 1, comprising a computer with computer readable software that, when executed, is configured to analyze colors of the plurality of colorimetric assay reaction pads to analyze the body fluid.

10. The on-diaper body fluid screening device according to claim 1, comprising a body fluid barrier network forming body fluid channels between an inlet section and the colorimetric assay reaction pads.

* * * * *